United States Patent [19]

Klein et al.

[11] 4,152,430

[45] May 1, 1979

[54] SYNERGISTIC COMPOSITIONS AND METHOD OF USE

[75] Inventors: Robert W. Klein, Blue Bell; George W. Nuss, Jr., Lansdale, both of Pa.

[73] Assignee: William H. Rorer, Inc., Fort Washington, Pa.

[21] Appl. No.: 835,595

[22] Filed: Sep. 22, 1977

[51] Int. Cl.² .................... A61K 31/44; A61K 31/555
[52] U.S. Cl. ..................................... 424/245; 424/263
[58] Field of Search .................. 424/263, DIG. 4, 245

[56] References Cited

U.S. PATENT DOCUMENTS

| 3,346,578 | 10/1967 | Langlykke et al. ................... 424/263 |
| 3,890,434 | 6/1975 | Weisse et al. .................. 424/DIG. 4 |
| 3,928,605 | 12/1975 | Curry ............................ 424/DIG. 4 |
| 4,049,665 | 9/1977 | Douglass ...................... 424/DIG. 4 |

Primary Examiner—Stanley J. Friedman

[57] ABSTRACT

The present invention relates to a novel synergistic composition and to a method of treating inflammation in warm blooded animals by topically administering to a warm blooded animal in need of such treatment an effective amount of the synergistic combination of a non-steroidal agent having anti-inflammatory activity and at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic acid and t is either 1 or 2.

20 Claims, No Drawings

SYNERGISTIC COMPOSITIONS AND METHOD OF USE

BACKGROUND OF THE INVENTION

The present invention relates to the novel method of treating inflammation in mammals by administering the synergistic combination of a non-steroidal agent having antiinflammatory activity and at least one metal salt of bis-2-pyridyl-1-oxide) disulfide and to novel compositions containing such compounds.

Bis-(2-pyridyl-1-oxide) disulfide (also referred to as 2,2'-dithiodipyridine-1-1'-dioxide) and various derivatives thereof, have previously been disclosed in the literature. For example, U.S. Pat. No. 2,742,476 discloses bis-(2-pyridyl-1-oxide) disulfide and the lower alkyl substituted derivatives thereof. U.S. Pat. No. 3,027,371 discloses molybdate derivatives, U.S. Pat. No. 3,027,732 discloses stannous chloride derivatives, and U.S. Pat. No. 3,346,578 discloses stannous fluoride derivatives of bis-(2-pyridyl-1-oxide) disulfide and each refer to the anti-fungal and antibacterial properties of said derivatives.

U.S. Pat. No. 3,890,434 discloses hair and antiseptic formulations containing adducts of bis-(2-pyridyl-1-oxide) disulfide with alkaline earth metal salts.

Co-pending application Ser. No. 835,594, of R. W. Klein et al relates to a composition and method for treatment of inflammation through the use of the synergistic combination of a corticosteroid and the metal salts of bis-(2-pyridyl-1-oxide) disulfide.

U.S. Pat. No. 3,600,437 discloses the preparation of α-methyl-3-phenoxybenzeneacetic acid.

U.S. Pat. Nos. 3,228,831 and 3,385,886 disclose the preparation of 4-(2-methylpropyl) benzeneacetic acid and α-methyl-4-(2-methylpropyl)benzeneacetic acid.

U.S. Pat. No. 3,637,776 discloses the preparation of α,2-(6-methoxy-2-naphthyl) propionic acid.

U.S. Pat. No. 3,161,654 discloses the preparation of 1-(p-chlorobenzoyl)-5-methoxy-α-methylindole-3-acetic acid.

U.S. Pat. No. 3,714,226 discloses the preparation of 2'4'-difluoro-4-hydroxy-3-biphenylcarboxylic acid.

DETAILED DESCRIPTION OF THE INVENTION

Now it has been found that even more pronounced pharmacological properties for the relief and inhibition of inflammation conditions can be provided by the topical administration of the combination of a non-steroidal agent having anti-inflammatory properties and the adducts of bis-(2-pyridyl-1-oxide) disulfide according to this invention. More specifically, these adducts have the formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2. More particularly, the anion Y is selected from the group consisting of halides, sulfates, nitrates, chlorates and acetates, with the chlorides and sulfates being most preferable. More particularly preferred are the water soluble adducts, especially calcium chloride ($CaCl_2$) or magnesium sulfate ($MgSO_4$). Also included in the adducts of this invention are the hydrates of the aforementioned compounds, i.e., adducts including $nH_2O$ groups where n is an integer of 0 to 10. Additionally, the adducts (I) may contain one or more substituents on either or both pyridine ring structures such as alkyls, halogens and alkoxy groups. It is further noted that $(C_5H_4NOS)_2$ as used in (I) above and throughout the specification and claims represents bis-(2-pyridyl-1-oxide) disulfide and the structural formula shown as follows:

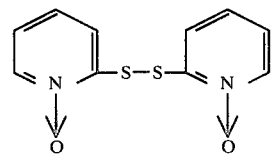

Among the active ingredients which may be utilized in combination with the non-steroidal agents having anti-inflammatory activity in this invention may be mentioned:

Bis-(2-pyridyl-1-oxide) disulfide magnesium sulfate, bis-(2-pyridyl-1-oxide) disulfide magnesium acetate, bis-(2-pyridyl-1-oxide) disulfide magnesium chloride, bis-(2-pyridyl-1-oxide) disulfide magnesium bromide, bis-(2-pyridyl-1-oxide) disulfide calcium chloride, bis-(2-pyridyl-1-oxide) disulfide calcium sulfate, bis-(2-pyridyl-1-oxide) disulfide calcium nitrate, bis-(2-pyridyl-1-oxide) disulfide calcium acetate, bis-(2-pyridyl-1-oxide) disulfide calcium chlorate, bis-(2-pyridyl-1-oxide) disulfide barium chloride, bis-(2-pyridyl-1-oxide) disulfide barium sulfate, bis-(2-pyridyl-1-oxide) disulfide barium nitrate, bis-(2-pyridyl-1-oxide) disulfide barium acetate, bis-(2-pyridyl-1-oxide) disulfide barium chlorate, bis-(2-pyridyl-1-oxide) disulfide strontium chloride, bis-(2-pyridyl-1-oxide) disulfide strontium sulfate, bis-(2-pyridyl-1-oxide)disulfide strontium nitrate, bis-(2-pyridyl-1-oxide) disulfide strontium acetate, bis-(2-pyridyl-1-oxide) disulfide strontium chlorate, bis-(2-pyridyl-1-oxide) disulfide potassium chloride, bis-(2-pyridyl-1-oxide) disulfide potassium sulfate, bis-(2-pyridyl-1-oxide) disulfide potassium nitrate, bis-(2-pyridyl-1-oxide) disulfide potassium acetate, bis-(2-pyridyl-1-oxide) disulfide potassium chlorate, bis-(2-pyridyl-1-oxide) disulfide sodium chloride, bis-(2-pyridyl-1-oxide) disulfide sodium sulfate, bis-(2-pyridyl-1-oxide) disulfide sodium nitrate, bis-(2-pyridyl-1-oxide) disulfide sodium acetate, bis-(2-pyridyl-1-oxide) disulfide sodium chlorate, bis-(2-pyridyl-1-oxide) disulfide zinc chloride, bis-(2-pyridyl-1-oxide) disulfide zinc sulfate, bis-(2-pyridyl-1-oxide) disulfide zinc nitrate, bis-(2-pyridyl-1-oxide) disulfide zinc acetate, bis-(2-pyridyl-1-oxide) disulfide zinc chlorate, bis-(2-pyridyl-1-oxide) disulfide stannous chloride, bis-(2-pyridyl-1-oxide) disulfide stannous sulfate, bis-(2-pyridyl-1-oxide) disulfide stannous nitrate, bis-(2-pyridyl-1-oxide) disulfide stannous acetate, bis-(2-pyridyl-1-oxide) disulfide stannous chlorate, bis-(2-pyridyl-1-oxide) disulfide zirconium chloride, bis-(2-pyridyl-1-oxide) disulfide zirconium sulfate, bis-(2-pyridyl-1-oxide) disulfide zirconium nitrate, bis-(2-pyridyl-1-oxide) disulfide zirconium acetate, bis-(2-pyridyl-1-oxide) disulfide zirconium chlorate, bis-(2-pyridyl-1-oxide) disulfide ferrous chloride, bis-(2-pyridyl-1-oxide) disulfide ferrous sulfate, bis-(2-pyridyl-1-oxide) disulfide ferrous nitrate, bis-(2-pyridyl-1-oxide) disulfide ferrous acetate, bis-(2-pyridyl-1-oxide) disulfide ferrous chlorate, bis-(2-pyridyl-1-oxide) disulfide lithium chloride, bis-(2-pyridyl-1-oxide) disulfide lithium sulfate, bis-(2-pyridyl-1-oxide) disulfide lithium nitrate, bis-(2-pyridyl-1-oxide) disulfide lithium acetate, and bis-(2-pyridyl-1-oxide) disulfide lithium chlorate.

A number of known effective anti-inflammatory non-steroidal agents may be utilized in this invention. Among the suitable non-steroidal agents may be mentioned 1-(p-chlorobenzoyl)-5-methoxy-2-methylindole-3-acetic acid d-2-(6-methoxy-2-naphthyl) propionic acid, 1-methyl-5-(4-methylbenzoyl-1 H-pyrrole-2-acetic acid, α-methyl-4-(2-methylpropyl) benzeneacetic acid, 4-(2-methylpropyl)benzeneacetic acid, α-methyl-3-phenoxybenzeneacetic acid, α, 3-dichloro-4-cyclohexylphenylacetic acid, 2'4'-difluoro-4-hydroxy-3-biphenylcarboxylic acid, and the like.

It has been surprisingly found that the anti-inflammatory activity of the adducts I is enhanced when combined with other known effective non-steroidal anti-inflammatory agents.

In accordance with the present invention, a method of treating inflammation in warm blooded animals is provided which comprises topically administering to a warm blooded animal in need of such treatment an effective amount of the combination of at least one of the aforementioned non-steroidal agents and the adducts of Formula I.

As used herein, the term "treatment" is meant to include both active treatment and preventative or prophylactic treatment.

The present invention also has for its object compositions and means for treating skin conditions requiring anti-inflammatory treatment such as contact dermatitis, seborrheic dermatitis, atopic dermatitis, neurodermatitis and the like, a composition containing the combination of a non-steroidal agent having anti-inflammatory activity and at least one of the adducts I in an amount of from about 0.05–10% by weight of the composition, preferably from about 0.25–5.0% by weight. The non-steroidal agents are utilized in the composition in an amount of 1–40% by weight of adduct I in the composition, preferably 5–25% by weight of adduct I present. These compositions can be in the form of a solution, a cream, powder, gel, ointment, salve, lotion, or milk. They can also constitute make-up products or dermatological cakes containing the ingredients standard to this type of composition.

The following Examples will further illustrate the formulations containing the non-steroidal agents and the adducts I but are not to be considered as limiting the scope of this invention.

EXAMPLE 1

| A cream was prepared as follows: | |
|---|---|
| Bis-(2-pyridyl-1-oxide) disulfide calcium chloride | 1 g |
| 1-(p-chlorobenzoyl)-5-methoxy-2-methylinole-3-acetic acid | 0.3 g |
| Titanium oxide | 10 g |
| Red iron oxide | 0.3 g |
| Yellow iron oxide | 0.2 g |
| Brown iron oxide | 0.4 g |
| Chestnut iron oxide | 0.2 g |
| Stearyl alcohols oxyethylenated with 33 moles of ethylene oxide | 7 g |
| Polyglycol stearate | 6 g |
| Propyl parahydroxybenzoate | 0.2 g |
| Water, Q.S.P. | 100 g |

Other creams identical to that described immediately above are prepared by replacing the calcium chloride compound with any of the previously mentioned active compounds.

EXAMPLE 2

A dermatological cleansing cake is prepared by mixing together the following components:

| | | |
|---|---|---|
| Esters of sodium isothionate and coprafatty acids (sold under the tradename "IGEPON A" having the formula R-COO-CH$_2$-CH$_2$-SO$_3$Na, wherein R equals fatty acid derivatives having 12–15 carbon atoms) | 75 | g |
| Lanolin derivatives | 22.75 | g |
| (C$_5$H$_4$NOS)$_2$ . MgCl$_2$ | 1 | g |
| d-2-(6-methoxy-2-naphthyl) propionic acid | 1 | g |

Other dermatological cleansing cakes, identical to the above, are prepared by replacing the magnesium chloride salt of bis-(2-pyridyl-1-oxide) disulfide with any one of the aforementioned active compounds. Also, any one of the non-steroidal acids mentioned may be utilized.

EXAMPLE 3

A powder comprising the following mixture:

| | | |
|---|---|---|
| Talc | 86.85 | g |
| Glycerine oleate | 3 | g |
| Isopropyl myristate | 7 | g |
| Bis-(2-pyridyl-1-oxide) disulfide magnesium sulfate | 1 | g |
| 1-methyl-5-(4-methylbenzoyl-1 H-pyrrole-2-acetic acid | 1 | g |
| Perfume | 2cc ($\approx$approx. 1.9g) | |

Other equally effective powder compositions identical to the above are prepared except that the active ingredient component bis-(2-pyridyl-1-oxide) disulfide magnesium sulfate is replaced by any of the other aforementioned active compounds.

EXAMPLE 4

Cocoa butter (approximately 40 g) is mixed with bis-(2-pyridyl-1-oxide) disulfide zinc acetate approximately 1 g and α-methyl-4-(2-methylpropyl)benzeneacetic acid (0.1) and the resulting mixture is melted with gentle heat and poured into a mold of suitable size and shape.

EXAMPLE 5

The following ointment base was utilized as a vehicle for the active ingredients of this invention:

| Ingredient | Amount in grams |
|---|---|
| Polyoxyethylene stearyl ether | 5.0 |
| White petrolatum | 5.0 |
| Stearyl alcohol | 15.0 |
| Distilled water | 63.5 |

The ointment containing the above active ingredients was manufactured in the following manner. 1.00 gram bis-(2-pyridyl-1-oxide) disulfide magnesium sulfate were dissolved in a heated mixture of 61.5 ml. of distilled water and 11.50 g of propylene glycol. This solution was heated to a temperature of 75° C. and added to a mixture having a like temperature consisting of 0.5 g of 4-(2-methylpropyl) benzeneacetic acid, 15.0 g of stearyl alcohol, 5.0 g of white petrolatum, 1.0 ml of concentrated ammonium solution and 5.0 g of polyoxyethylene stearyl ether, molecular weight about 700. While the resulting mixture was still hot, lactic acid was added to adjust the pH thereof to about 5.5 to approximate the pH of skin. The resulting mixture was thereafter cooled to form a cream which was further worked utilizing a three-roller frame and filled into tubes.

In an analogous manner, ointments with 4-(2-methylpropyl) benzeneacetic acid were prepared utilizing the following ingredients to form the initial solutions:

a. 4.27 grams bis-(2-pyridyl-1-oxide) disulfide ferrous chloride in 53.23 ml of distilled water and 11.5 g of propylene glycol;

b. 4.51 grams of bis-(2-pyridyl-1-oxide) disulfide lithium acetate in 56.19 ml of distilled water and 11.5 g of propylene glycol;

c. 4.62 grams of bis-(2-pyridyl-1-oxide) disulfide zirconium chloride in 56.35 ml of distilled water and 11.5 g of propylene glycol;

d. 2.0 grams of bis-(2-pyridyl-1-oxide) disulfide strontium chloride in 60.7 ml of distilled water and 11.5 g of propylene glycol.

In this example the solution was heated to 75° C. and added to a mixture having a like temperature and containing 4.5 grams of bis-(2-pyridyl-1-oxide) disulfide magnesium sulfate, 0.45 α-methyl-3-phenoxybenzeneacetic acid, 13.0 grams of stearyl alcohol, 5.0 grams of polyoxyethylene stearyl ether, molecular weight about 700 and 5.0 grams of white petrolatum, the pH was adjusted with lactic acid and the mixture cooled to form a cream which was worked up as above.

EXAMPLE 6

An ointment was prepared by first mixing 2.0 g of bis-(2-pyridyl-1-oxide) disulfide magnesium sulfate, 2.0 g of bis-(2-pyridyl-1-oxide) disulfide magnesium chloride and 1.0 g of α-3,-dichloro-4-cyclohexylphenylacetic acid in a hot mixture of 57.5 g of distilled water and 11.5 g of propylene glycol.

EXAMPLE 7

An aerosol preparation was formed from the following formulation:

| Phase I | |
|---|---|
| Ingredient | Weight in grams |
| Isopropyl myristate | 18 |
| Stearic acid, cosmetic grade | 30 |
| Myristic acid, cosmetic grade | 9 |
| Glycerin | 18 |
| Phase II | |
| Ingredient | Weight in grams |
| Water | 440 |
| Triethanolamine | 20 |
| Bis-(2-pyridyl-1-oxide) disulfide calcium chloride | 22 |
| Phase III | |
| Ingredient | Weight in grams |
| Panthenol | 6 |
| Suitable perfume | 3 |
| 2,4'-difluoro-4-hydroxy-3-biphenylcarboxylic acid | 12 |
| Lactic acid q.s.pH | 5.5 |

Phase I and Phase II were separately heated at a temperature of about 75° C. Thereafter, Phase II was added dropwise with vigorous stirring to Phase I which was maintained at a temperture of 75° C. The mixture was then cooled to above 50° C. with stirring and the first three ingredients of Phase III added thereto. The resulting emulsion was mixed and the pH adjusted to about 5.5 with lactic acid. The emulsion was then cooled with stirring to about 20° C.

Nine parts by weight of the emulsion formed above were combined with one part by weight of a propellant (40 dichlorodifluoromethane/60 dichlorotetrafluoroethane) under pressure in suitable aerosol container equipped with conventional valve apparatus and foam-forming head.

EXAMPLE 8

An anti-inflammatory composition in milk form having the following composition:

| Ingredient | Weight in grams |
|---|---|
| Hydrogenated, ethoxylated (10 mol) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| α,3-dichloro-4-cyclohexyl-phenylacetic acid | 0.75 |
| Stearic acid | 3.0 |
| Bis-(2-pyridyl-1-oxide) disulfide magnesium sulfate | 2.0 |
| Demineralized water | 72.2 |
| Triethanolamine | 0.8 |
| Perfume | 0.5 |
| Carboxyvinylpolymer 941 | 1.0 |
| Conservation agent | 2.0 | was manufactured as follows:

A mixture of 1.8 g hydrogenated, ethoxylated (10 mol) lanolin, 7.0 g triglyceride of fatty acid of coconut, 0.6 g cetylalcohol, 0.6 g stearyl alcohol, 5.0 g paraffin oil, 0.75 g α,3-dichloro-4-cyclohexylphenylacetic acid and 3.0 g of stearic was blended at 70° C. After addition of 4.0 g bis-(2-pyridyl-1-oxide) disulfide magnesium sulfate, 2.0 g carboxyvinylpolymer in 72.2 g demineralized water were added at 70° C. with stirring to the resulting suspension. The mixture was stirred for 15 minutes and then cooled to 50° C. The 0.8 g of triethanolamine and 0.5 g of perfume were added at 50° C. and 45° C. respectively. The resulting mixture was stirred until cold and a white mile was obtained. Viscosity: 4,000 Cp (Brookfield, Spindel, 5 at 10 Rpm).

EXAMPLE 9

0.5 g of bis-(2-pyridyl-1-oxide) disulfide magnesium sulfate and 0.5 g α-methyl-3-phenoxybenzeneacetic acid are predispersed in 30.0 g of propylene glycol. The mixture is then homogenized into 99.0 grams of finished cream, ointment or lotion, following a modification of any one of the procedures of Examples 2, 6 and 7 or as described in F. W. Martin et al, "Remington's Pharmaceutical Sciences", 14th Ed., Mack Publishing Co., Easton, Pa., 1965.

Other agents which have either medicinal, therapeutic or cosmetic value may be incorporated in the compositions of this invention.

I claim:

1. A method of treating inflammation in warm blooded animals which comprises topically administering to a warm blooded animal in need of such treatment an effective amount of 1-(p-chlorobenzoyl)-5-methoxy-2-methylindole-3-acetic acid and at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, tin, cadmium, magnesium, zirconium, alkali and alkaline earth metals; Y is the anion of an inorganic or organic acid and t is either 1 or 2, said 1-(p-chlorobenzoyl)-5-methoxy-2-methylindole-3-acetic acid being present in the amount of 1–40% by weight of said adduct.

2. The method of claim 1, wherein M is magnesium, Y is sulfate and t is 1.

3. The method of claim 1, wherein M is calcium, Y is chloride and t is 2.

4. The method of claim 1, wherein M is calcium, magnesium or barium.

5. The method of claim 1, wherein the formula is selected from the group consisting of $(C_5H_4NOS)_2CaCl_2$, $(C_5H_4NOS)_2MgSO_4$, $(C_5H_4NOS)_2SrCl_2$, $(C_5H_4NOS)_2SrBr_2$, $(C_5H_4NOS)_2 Ca(NO_3)_2$ and $(C_5H_4NOS)_2Ba(ClO_3)_2$.

6. The method of claim 1, wherein said warm blooded animal is treated for skin conditions requiring anti-inflammatory treatment.

7. The method of claim 6, wherein said skin condition is contact dermatitis, seborrheic dermatitis, atopic dermatitis or neuro dermatitis.

8. The method of claim 1, wherein said adducts are water-soluble.

9. The method of claim 1, wherein Y is selected from the group consisting of halides, sulfates, nitrates and acetates.

10. A method for treating inflammation in warm blooded animals which comprises topically administering to a warm blooded animal in need of treatment, a pharmaceutical composition containing 0.05–10% by weight of the combination of α,3-dichloro-4-cyclohexylphenylacetic acid and bis-(2-pyridyl-1-oxide) disulfide magnesium sulfate, said α,3-dichloro-4-cyclohexylphenylacetic acid being present in an amount of 1–40% by weight of bis-(2-pyridyl-1-oxide) disulfide magnesium sulfate.

11. A method of treating inflammation in warm blooded animals which comprises topically administering to a warm blooded animal in need of such treatment an effective amount of a non-steroidal anti-inflammatory agent selected from the group consisting of 1-(p-chlorobenzoyl)-5-methoxy-2-methylindole-3-acetic acid, d-2-(6-methoxy-2-naphthyl) propionic acid, 1-methyl-5-(4-methylbenzoyl-1 H-pyrrole)-2-acetic acid, α-methyl-4-(2-methylpropyl)benzeneacetic acid, 4-(2-methylpropyl)benzeneacetic acid, α-methyl-3-phenoxybenzeneacetic acid, α,3-dichloro-4-cyclohexylphenylacetic acid and 2',4'-difluoro-4-hydroxy-3-biphenylcarboxylic acid, and at least one adduct of bis-(2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2, said non-steroidal anti-inflammatory agent being present in the amount of 1–40% by weight of said adduct.

12. A composition for topically treating inflammation in warm blooded animals which comprises about 0.05 to about 5% by weight of the total composition of the combination of a non-steroidal anti-inflammatory agent selected from the group consisting of 1-(p-chlorobenzoyl)-5-methoxy-2-methylindole-3-acetic acid, d-2-(6-methoxy-2-naphthyl) propionic acid, 1-methyl-5-(4-methylbenzoyl-1 H-pyrrole)-2-acetic acid, α-methyl-4-(2-methylpropyl)benzeneacetic acid, 4-(2-methylpropyl) benzeneacetic acid, α-methyl-3-phenoxybenzeneacetic acid, α,3-dichloro-4-cyclohexylphenylacetic acid and 2',4'-difluoro-4-hydroxy-3-biphenylcarboxylic acid and the adducts of bis-([-]2-pyridyl-1-oxide) disulfide having the empirical formula:

$$(C_5H_4NOS)_2MY_t \qquad (I)$$

wherein M represents a member selected from the group consisting of zinc, iron, magnesium, tin, cadmium, zirconium, alkali and alkaline earth metals; Y is the anion of an inorganic or organic acid and t is either 1 or 2, together with a suitable pharmaceutical carrier, said non-steroidal anti-inflammatory agent being present in the amount of 1–40% by weight of said adduct.

13. A composition for topically treating inflammation in warm blooded animals which comprises about 0.05 to about 5% by weight of the total composition of the combination of 1-(p-chlorobenzoyl)-5-methoxy-2-methylindole-3-acetic acid and the adducts of bis-([≡]2-pyridyl-1-oxide) disulfide having the empirical formula:

$$(C_5H_4NOS)_2MY_t \qquad (I)$$

wherein M represents a member selected from the group consisting of zinc, iron, tin, cadmium, magnesium, zirconium, alkali and alkaline earth metals; Y is the anion of an inorganic or organic acid and t is either 1 or 2, together with a suitable pharmaceutical carrier, said 1-(p-chlorobenzoyl)-5-methoxy-2-methylindole-3-acetic acid being present in the amount of 1–40% by weight of said adduct.

14. The composition of claim 13, wherein M is magnesium, Y is sulfate and t is 1.

15. The composition of claim 13, wherein M is calcium, Y is chloride and t is 2.

16. The composition of claim 13, wherein M is calcium, magnesium or barium.

17. The composition of claim 13, wherein the formula is selected from the group consisting of $(C_5H_4NOS)_2CaCl_2$, $(C_5H_4NOS)_2MgSO_4$, $(C_5H_4NOS)_2SrCl_2$, $(C_5H_4NOS)_2SrBr_2$, $(C_5H_4NOS)_2Ca(NO_3)_2$ and $(C_5H_4NOS)_2Ba(ClO_3)_2$.

18. The composition of claim 13, wherein said adducts are water-soluble.

19. The composition of claim 13, wherein Y is selected from the group consisting of halides, sulfates, nitrates and acetates.

20. A composition for topically treating inflammation in warm blooded animals comprising as active agents the combination of α,3-dichloro-4-cyclohexylphenylacetic acid and bis-(2-pyridyl-1-oxide) disulfide magnesium sulfate and a suitable pharmaceutical carrier, said active agents being present in said composition in an amount of 0.05–10% by weight of composition and said α,3-dichloro-4-cyclohexylphenylacetic acid being present in an amount of 1–40% by weight of bis-(2-pyridyl-1-oxide) disulfide magnesium sulfate.

* * * * *